(12) United States Patent
Sioli

(10) Patent No.: US 8,779,130 B2
(45) Date of Patent: Jul. 15, 2014

(54) PROCESS FOR PRODUCING HIGH-QUALITY MELAMINE FROM UREA

(75) Inventor: Giancarlo Sioli, Cernobbio (IT)

(73) Assignee: Urea Casale SA (CH)

( * ) Notice: Subject to any disclaimer, the term of this patent is extended or adjusted under 35 U.S.C. 154(b) by 512 days.

(21) Appl. No.: 12/922,982

(22) PCT Filed: May 14, 2009

(86) PCT No.: PCT/EP2009/055825
§ 371 (c)(1),
(2), (4) Date: Sep. 16, 2010

(87) PCT Pub. No.: WO2009/138450
PCT Pub. Date: Nov. 19, 2009

(65) Prior Publication Data
US 2011/0054169 A1   Mar. 3, 2011

(30) Foreign Application Priority Data
May 14, 2008   (EP) .................................... 08008958

(51) Int. Cl.
*C07D 251/60* (2006.01)
*C07D 251/62* (2006.01)

(52) U.S. Cl.
USPC .......................................... 544/201; 544/203

(58) Field of Classification Search
USPC ................................................. 544/201, 203
See application file for complete search history.

(56) References Cited

U.S. PATENT DOCUMENTS

| | | | |
|---|---|---|---|
| 4,565,867 A | 1/1986 | Thomas et al. | |
| 6,258,950 B1 | 7/2001 | van Wijck | |
| 6,870,050 B2 * | 3/2005 | Coufal et al. | 544/201 |
| 2004/0171831 A1 | 9/2004 | Tjioe et al. | |
| 2005/0056147 A1 | 3/2005 | Schroder et al. | |
| 2005/0119483 A1 | 6/2005 | Coufal | |
| 2005/0288529 A1 | 12/2005 | Tjioe et al. | |
| 2006/0100428 A1 | 5/2006 | Tjioe et al. | |
| 2007/0232801 A1 | 10/2007 | Bairamijamal | |

FOREIGN PATENT DOCUMENTS

| | | |
|---|---|---|
| CN | 1446808 A | 10/2003 |
| WO | 2004/085413 A1 | 10/2004 |
| WO | 2004/096782 A1 | 11/2004 |

* cited by examiner

Primary Examiner — Kamal Saeed
Assistant Examiner — Ebenezer O Sackey
(74) Attorney, Agent, or Firm — Akerman LLP

(57) ABSTRACT

A process for high-pressure, liquid phase conversion of urea into melamine is disclosed, where molten urea is fed to a first reaction zone (S1) where the melamine melt is under mechanical agitation, and a heat input (Q1) is provided to maintain the endothermic reaction, and the liquid is then passed to a second reaction zone (S2) kept at a lower temperature and where further agitation is provided. Embodiments of plants adapted to carry out the process are also disclosed, including multiple stirred reactors in cascade and a single reactor with multiple internal compartments defining said first and second reaction zones.

17 Claims, 6 Drawing Sheets

PROCESS FOR PRODUCING HIGH-QUALITY MELAMINE FROM UREA

FIELD OF THE INVENTION

The invention relates to a process for converting urea into melamine in a high-pressure liquid phase, and to a reactor or a system of reactors for carrying out the inventive process.

PRIOR ART

Melamine ($C_3H_6N_6$) is industrially produced from urea, by a strongly endothermic chemical reaction, at temperature about 400° C., that can be summarized as follows:

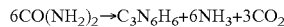

$$6CO(NH_2)_2 \rightarrow C_3H_6N_6 + 6NH_3 + 3CO_2$$

i.e. six moles of urea are converted into one mole of melamine plus ammonia and carbon dioxide. Melamine users require a commercial product of very high purity, usually not less than 99.8%, so that the process must be developed in order to remove impurities and avoid as much as possible the formation of by-products.

The known art basically provides two processes for carrying out the above reaction, namely the low-pressure process, usually below 10 bar, and in presence of catalysts (catalyzed gas-phase process), and the high-pressure liquid phase process, where conversion takes place in liquid phase and pressure is usually in the range from 70 to 200 bar. Both the low-pressure and high-pressure process are well known; in recent years there has been a growing interest in the high-pressure process as simpler and less energy-intensive.

The high-pressure process takes place in a liquid phase and inside an appropriate reactor. The reactor is substantially a pressure vessel, designed to withstand the high temperature and pressure, as well as the severe corrosion problems; the reactor is also equipped with appropriate means to supply the large amount of heat required by the reaction, usually around 240 kJ/kg of produced melamine.

In the steady-state conditions, the liquid phase contained in the reactor has a substantially uniform composition, usually 88-92% wt of melamine; 4-5% wt of melamine precursors (mainly comprising cyanuric acid, ammelide and ammeline) and melamine poly-condensates (melem, melam); 4-5% wt of unconverted urea, the balance being due to dissolved ammonia and carbon dioxide. This liquid phase is generally recalled as "melamine melt". Said melamine melt is taken from the reactor and transferred to subsequent stages for obtaining pure melamine (99.8% or more).

A liquid urea stream is continuously added to said melamine melt (liquid phase) contained in the reactor. Some gaseous ammonia is also bubbled through the reactor liquid, with the aim of minimizing the possible formation of melamine poly-condensates and of preventing the formation of some urea infusible compounds. The surplus ammonia is also re-used, outside the melamine plant, for the production of urea.

Ammonia and carbon dioxide are taken as a gaseous stream entraining some melamine and melamine precursors, which are generally recovered by scrubbing with the urea reactor feed. Evolved gases are collected, purified, and generally recovered as starting material for the further production of urea.

An example of a reactor operating with the high-pressure liquid phase process is disclosed in U.S. Pat. No. 4,565,867.

The main technical problems presented by the high-pressure liquid phase process herein considered can be summarized as follows.

First, there is the need of a large heat exchange surface for supplying the relevant reaction heat, and a there is an effort to realise the highest heat transfer surface per unit reaction mass. The common situation in the prior art is that the overall volume of the reactor is determined by the size of the heat exchanger, rather than by the residence time required to carry out the urea conversion. Another problem is the need of a good and immediate dispersion of urea in the hot melamine melt, to avoid formation of infusible by-products; the urea feed must also be converted as much as possible, to minimise the unconverted urea content in the melamine. Furthermore, there is the need of using efficiently the added ammonia, which reduces the formation of melamine poly-condensates, but adds up to the off gas to be recovered and recycled to the urea synthesis process.

The above problems are highly felt in consideration of the high purity of the requested melamine end-product and, despite several efforts, the prior art does not provide yet a satisfactory solution.

SUMMARY OF THE INVENTION

The problem underlying the present invention is to improve the known high-pressure liquid phase process for conversion of urea into melamine, solving the problems listed above.

The problem is solved by a process for converting urea into melamine at a high-pressure and in a liquid phase, where a liquid stream comprising molten urea is fed to a liquid melamine melt where conversion takes place, the process being characterized in that:

said liquid stream comprising molten urea is fed to a first reaction zone, where the melamine melt is kept under mechanical agitation, and a heat input is provided to the first reaction zone;

a liquid phase comprising melamine is taken from said first reaction zone and fed to a subsequent second reaction zone, where liquid phase is kept under mechanical agitation, the temperature of the liquid phase in said second reaction zone being lower than temperature of the liquid phase in said first zone.

It should be noted that the terms first reaction zone and second reaction zone may, according to embodiments of the invention, relate to different internal compartments or group of internal compartments of a single vessel, or to different reactors, or groups of reactors forming a first stage and a second stage, respectively, for conversion of urea into melamine. This will further explained herein below with the help of examples.

The difference between the temperature in the first reaction zone and the lower temperature in the second zone, in a preferred realization, is ranging from 40-50° C. to 60-120° C., and is preferably around 50-70° C. Preferably, the temperature of the liquid phase in the first zone is in the range from 360 to 440° C., more preferably in the range from 380 to 420° C., while the temperature of the liquid phase in the second zone is in the range from 320 to 390° C., more preferably in the range from 330 to 350° C.

According to one embodiment of the invention, a heat removal is provided from the second reaction zone to obtain in said reaction zone a temperature of the liquid mass lower than in the first reaction zone. For example heat is continuously removed by a cooling medium flowing in a coil or other heat exchanger immersed in the liquid phase. According to another embodiment, the liquid mass is cooled during the passage from the first reaction zone to the second reaction zone, and said second reaction zone operates in a substantially adiabatic manner.

The heat supply to the first reaction zone can be obtained as well with a heat exchanger, fed with a suitable heating medium. An electric heater can also be used to provide heat to the first reaction zone.

According to a further aspect of the invention, the operating pressure of the second reaction zone is greater than pressure in the first reaction zone. In preferred embodiments, the first reaction zone is at 50 to 250 bar, more preferably 70 to 170 bar, while the second reaction zone is at 100 to 300 bar and more preferably at 150 to 250 bar. In other embodiments, the first and second reaction zone are substantially at the same pressure.

According to another aspect of the invention, the mechanical agitation is provided in the so-called fully-baffled condition of the liquid phase, in at least one of the first and second reaction zone, and preferably in both zones. Fully-baffled condition is defined, as usual in the related literature, as the condition where the tangential entrainment of liquid is impeded, for example by appropriate baffles, and the cylindrically rotating vortex disappears, allowing transfer of a significant deal of power to the liquid under agitation. Mechanical agitation is provided for example with one or more impellers and preferably the power input from the mechanical agitator(s) to the liquid phase is 0.1 to 10 kW per cubic meter of un-gassed liquid, more preferably 0.5 to 5 kW.

In a further aspect of the invention, gaseous ammonia is added to at least one of the liquid phase of said first reaction zone and the liquid phase of said second reaction zone, said gaseous ammonia being added to the same zone where the mechanical agitation is transferred to said liquid phase, that is, for example, near the rotating blades of an agitator provided to this purpose. Preferably, also the liquid stream comprising molten urea is added to the liquid phase in the region where the mechanical agitation is transferred to said liquid phase.

Gaseous ammonia is preferably added to the liquid phase contained in both the first reaction zone and second reaction zone, near the blades (or equivalent) of the agitator; adding ammonia in this region of the liquid phase is preferred to obtain best mixing of the gaseous ammonia into the liquid.

A gaseous stream mainly consisting of carbon dioxide and ammonia, plus excess of the added ammonia and some melamine and intermediate reaction products, is taken from both the first and the second reaction zone. Preferably the gaseous stream from the first reaction zone and the gaseous stream from the second reaction zone are kept separate, i.e. they are not mixed.

The invention is also directed to a reactor or a system of reactors adapted to carry out the above process. More in detail, an object of the invention is an equipment for carrying out the above process, comprising at least one high-pressure vessel, said equipment providing a first reaction zone and a second reaction zone and comprising at least:
- a flow line adapted to feed a liquid stream comprising molten urea to said first reaction zone;
- at least a mechanical agitator operating in said first reaction zone and heating means adapted to provide heat to said first reaction zone;
- a flow path adapted to receive liquid phase from said first reaction space and feed said liquid phase to the second reaction space,
- at least a further mechanical agitator operating in said second reaction zone, and cooling means adapted to provide that temperature of the liquid phase in the second reaction zone is lower than temperature of the liquid phase in the first reaction zone.

In one embodiment, the first and second reaction zone are obtained with at least a first and a second vessel, respectively. In another embodiment, the first and/or the second reaction zone are defined by multiple vessels. Each vessel of a multi-vessel arrangement can be further multi-compartmented. In another embodiment, a single vessel has at least one internal compartment providing the first reaction zone and at least another compartment providing the second reaction zone. A single vessel can also comprise multiple compartments, e.g. in cascade, for the first reaction zone and/or for the second reaction zone. In all above embodiments the vessel(s) can be vertical or horizontal. Preferably, each vessel or compartment has a respective mechanical agitator.

Said heating means and cooling means, in one embodiment, are represented by heat exchangers accommodated in the respective vessels or compartments and fed respectively with a heating and a cooling medium. The heat exchange medium can be fed in parallel to respective heat exchangers of multiple vessels or compartments. In another embodiment, a heat exchanger (cooler) for cooling the liquid phase can be installed on said flow path carrying the liquid phase from the first to the second reaction zone.

Multiple compartments inside a single vessel, as well as multiple vessels, can be arranged in cascade, that is with the liquid phase flowing by gravity from a generic compartment or vessel to the subsequent compartment or vessel. In alternative embodiments, pumping means are provided to feed the liquid between said compartments or vessels. In particular, if the second reaction zone, or second stage, is run at a greater pressure than the first stage, said flow path comprises a pump.

Examples of embodiments of an equipment for carrying out the process are as follows.

In a first embodiment, the equipment comprises two separate stirred reactors arranged in cascade, namely a first reactor providing the first reaction zone and a second reactor providing the second reaction zone. Each reactor is equipped with a mechanical agitator; the first vessel is also equipped with a heating coil fed with a heating fluid, or electric in alternative, while the second vessel is equipped with a heat exchanger fed with a cooling fluid. In operation, the liquid urea is fed to the first reactor and liquid melamine melt is passed from the first to the second reactor by gravity or via a feeding pump.

In a second embodiment, the equipment comprises a single horizontal reactor, providing a first internal compartment for the first reaction zone and a second internal compartment for the second reaction zone. Said compartments are separated by internal baffles defining a weir, with a passage for the liquid phase to flow by gravity from the first to the second compartment. Each compartment is equipped with a mechanical agitator; a heater is accommodated in the first compartment and a cooling heat exchanger is accommodated in the second compartment. In operation, liquid urea is fed to the first compartment and melamine melt passes to the second compartment via said weir and passage.

In a third embodiment, the equipment comprises a cascade of stirred vertical reactors, each having a separate vessel. Three vertical reactors for example provide the first reaction zone (first stage), and two further vertical reactors form the second reaction zone (second stage). Each reactor is equipped with a respective internal mechanical agitator and a heat exchanger, providing or removing heat respectively in reactors of the first or second stage. A heating medium and a cooling medium are fed and collected in parallel to/from heat exchangers of reactors of first and second stage. Liquid urea is fed to the top reactor of the first stage and the melamine melt passes from the last reactor of the first stage to the first reactor of the second stage, by gravity or with a feeding pump.

In a fourth embodiment, the equipment comprises two multi-compartmented horizontal reactors, the first reactor comprising a cascade of multiple compartments providing the first reaction zone, and the second reactor providing a cascade of multiple compartments for the second reaction zone. Each single compartment is equipped with a mechanical agitator and a respective heat exchanger, furnishing or removing heat respectively in the first and second zone or stage. Urea is fed to the top compartment of the first reactor.

In a fifth embodiment, the equipment comprises a single horizontal vessel containing a cascade of multiple compartments, wherein a first group of said compartments form the first stage, i.e. provides the first reaction zone, and a second group of said compartments form the second stage, i.e. provides the second reaction zone. Each compartment has an agitator and a heat exchanger, as described above.

As apparent to the skilled person, other equivalent embodiments are possible, with multiple vessels, compartmented vessels or any combination thereof.

In all above embodiments, a further ammonia feed is preferably provided to the liquid phase contained in all reactors or compartments of the first stage. When multiple reactors or compartments are provided, ammonia is preferably fed in parallel to each of them; gaseous ammonia and carbon dioxide are taken from top of all reactors or compartments, as the case may be.

In those embodiments where the first and second reaction zone are obtained with separate pressure vessels, the second zone can be advantageously operated at a pressure higher than the first zone. In this case, a pump is provided to transfer the liquid melamine melt from the first stage to the second stage. For example, in a variant of the first embodiment as discussed above, the second reactor is operated at a greater pressure and liquid is pumped, instead of flowing by gravity, from the first to the second reactor.

The mechanical agitators are preferably impellers with a magnetic driving, which is per se known, to avoid the problem of sealing the agitators. To promote the full-baffled condition of the liquid phase, each of said vessel, or each of said compartments, is provided with internal vertical baffles, to impede the rotation of the agitated liquid mass, enhancing the shear effect of the impeller and therefore the mass and heat transfer rates. In still preferred embodiments, the melted urea is fed near and above the blades of the impeller of the first stage, while added gaseous ammonia is fed below the blades of impellers of the first and second stage.

The above two-stage conversion process has been found surprisingly efficient. Due to the mechanical agitation and the feed of molten urea to the first stage, the molten urea is dispersed in the reaction mass in a very effective manner and instantaneously, avoiding the formation of infusible products. Moreover, also the added ammonia is distributed in the reaction mass in a highly efficient way, due to the feeding in the region where mechanical agitation is imparted to the liquid mass, and the liquid mass itself is under intense agitation, thus obtaining a larger gas-liquid interface than in prior-art, maximizing the transformation of melamine precursors into melamine, and minimizing the formation of melamine polycondensates, with the result of producing a melamine melt highly concentrated in melamine.

The heat exchange at process side, which is usually limiting the overall heat supply to the reacting mass, is substantially enhanced, reducing the extension of the heat exchange surface, and the reactor volume at equality of urea conversion per unit time.

The conversion degree of urea, without changing the operation temperature with respect to the know art, is increased and, as it will be shown hereinafter, may be carried to practical completion.

The result is almost complete absence of infusible urea derivatives, a very intensive heat supply, due to a process-side heat transfer coefficient more than twice the one obtained with the best gas lift, a very efficient contact of ammonia with the reacting liquid, where the interfacial area per unit volume is at least tenfold the one created by the simple, gravity-driven gassing rate in the reactors of the prior art.

The invention allows to obtain higher purity of the melamine end-product and, hence, a more valuable product.

The invention is now described in further detail with reference to preferred and non-limiting embodiments and with the help of the drawings.

DETAILED DESCRIPTION OF THE INVENTION

Figure 1:
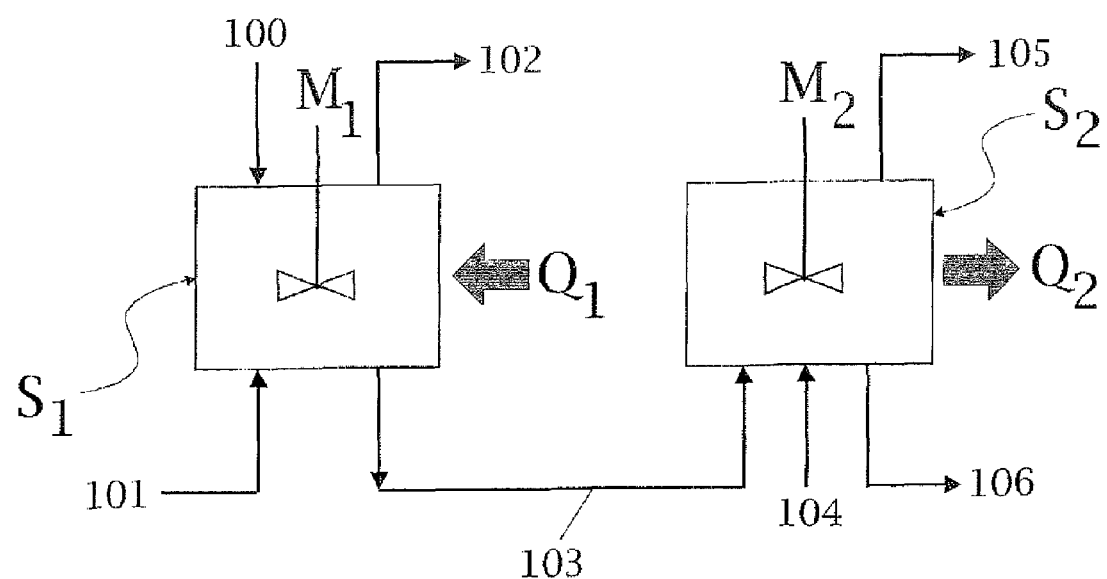
FIG. 1 is a block diagram of a process for converting urea into melamine according to the invention.

Referring to FIG. 1, a high-pressure liquid phase conversion of urea into melamine is carried out with a first step in a first reaction zone S1, followed by a second step in a second reaction zone S2. A liquid stream 100 comprising molten urea is fed to the first zone S1, where a melamine melt in liquid phase is maintained in agitation by a suitable agitator M1. A gaseous ammonia stream 101 is added to said reaction zone S1. A heat input Q1 is also provided to said reaction zone S1 by appropriate means, e.g. an electric heater or a heat exchanger fed with a heating medium, to maintain the endothermic reaction of conversion of urea into melamine.

The liquid phase, containing melamine, is taken from reaction zone S1 and passed to the second reaction zone S2 via line 103. Temperature of liquid phase in the second reaction zone S2 is lower than temperature of the liquid phase in first zone S1; pressure of the zone S2 may be substantially the same or higher and, in this last case, a pump is provided on line 103. The liquid phase in second zone S2 is maintained in agitation by a suitable agitator M2, and a heat Q2 is removed from said second zone S2, e.g. via a heat exchanger fed with a cooling medium. The second zone S2 also receives gaseous ammonia 104. In another embodiment (not shown), the heat Q2 can be removed on the path of line 103, e.g. by a heat exchanger between zones S1 and S2, the reaction zone S2 operating then in adiabatic regime.

For example, the first zone S1 is run at about 380-420° C. and 70-170 bar; the second zone S2 is run at a lower temperature, e.g. 330-350° C.; pressure in the second zone S2 is the same or higher.

High-purity liquid melamine is obtained at 106, while gaseous phase, mainly consisting of ammonia and carbon dioxide, is vented from reaction zones S1 and S2 via lines 102 and 105 respectively.

The first reaction zone S1 and the second reaction zone S2 can be obtained with respective stirred high-pressure reactor vessel and/or multiple stirred compartments of a larger reactor vessel. Some preferred embodiments are presented below with reference to FIGS. 2A, 2B and 3 to 6.

First Embodiment

Figure 2A:
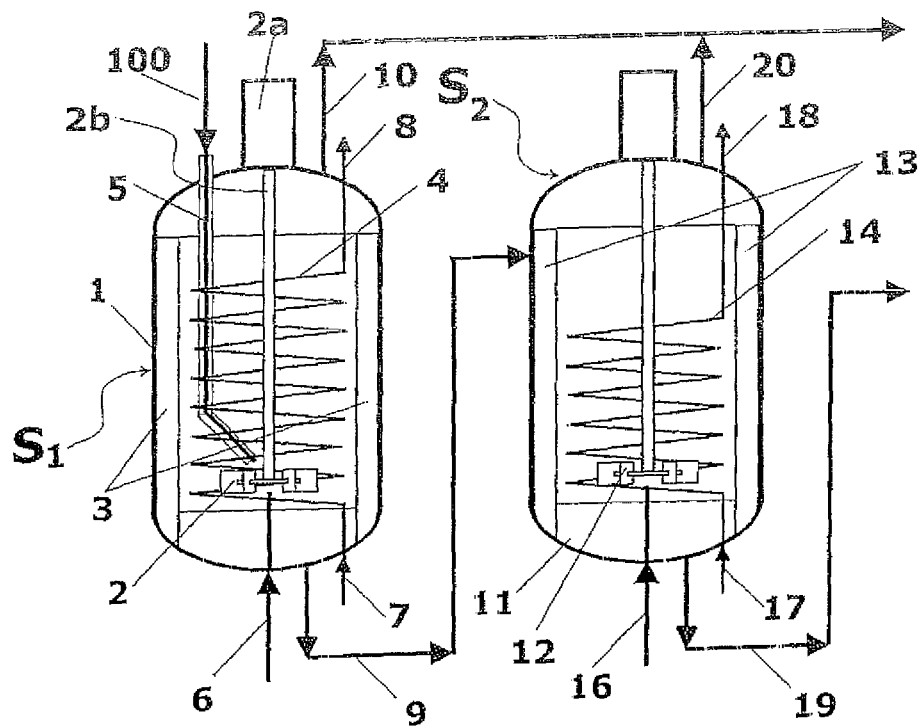
FIG. 2A is a scheme of an equipment in accordance with one embodiment of the invention, comprising a cascade of two stirred reactors for a first stage and a second stage of conversion of urea into melamine.

Referring to FIG. 2A, reaction zones S1 and S2 are obtained with a first stirred vessel 1 and a second stirred vessel 11 connected by a melamine melt line 9. Molten urea feed 100 is introduced via urea duct 5 into the first vessel 1. Further ammonia (streams 101, 104 of FIG. 1) is added via lines 6 and 16 to the liquid phase in both vessels 1 and 11. Gaseous products, mainly comprising ammonia and $CO_2$, are collected at lines 10 and 20, respectively. Melamine melt is obtained at line 19, i.e. at the output of the second vessel 11.

The vessel 1 is provided with a mechanical impeller 2, and vertical baffles 3 to maintain agitation of the liquid phase. The impeller 2 has a driving motor 2a and a shaft 2b extending inside the vessel 1. Said baffles 3 are appropriate to realize a "fully baffled condition", where the tangential entrainment of liquid is impeded, and the cylindrically rotating vortex disappears, allowing transfer of a significant deal of power to the liquid under agitation. The impeller 2 may be e.g. a turbine or a propeller; a flat-blades turbine is however preferred. The impeller 2 is preferably a magnetically-driven machine, which eliminate the problem of sealing the driving shaft.

The vessel 1 is also provided with heat transfer coils 4, which may be realised as pipes internally crossed by a heating fluid, as for instance by a stream of molten salts, fed by a pipe 7 and discharged by a pipe 8, or as an electric heater in form of coil. In order to exploit efficiently the heat transfer conditions, in connection to the mechanical agitation, the coil assembly must not prevent the liquid circulation imparted by the agitator, and therefore the power input to the liquid phase. Some expedients are taken thereof, as for instance by keeping the outer coil bank sufficiently away from the shell of the vessel, by keeping a reasonable clearance between two adjacent coil banks and between successive coils, by not staggering the coils, by limiting the number of banks to no more than three or four.

Molten urea stream 100 may contain also some melamine and melamine precursors, recovered by scrubbing of the reaction off gases with fresh urea, as customary in many processes of the known art. In a preferred embodiment, the open end of urea pipe 5 is located near to the central-top proximity of the agitator impeller 2, as shown; in this way, as soon as urea arrives to the upper part of the impeller 2, it is immediately dispersed inside the liquid phase present in the vessel 1.

A preferred realisation provides insulation of the urea pipe 5. Said insulation can be provided for example with a non-conductive thermal layer, or with a pipe jacket filled with diatomite or alike, or by a pipe jacket under vacuum, or by circulating in the jacket an appropriate fluid with low heat conductivity, as for instance a gas or superheated steam.

Gaseous, preheated ammonia is fed via the line 6, preferably with an ammonia feeding pipe extending inside the vessel 1 until the central, lower part of the agitator impeller. As soon as ammonia arrives to the lower part of the agitator impeller, it is immediately subdivided into very fine droplets, and dispersed inside the liquid phase present in the vessel 1. In operating conditions the power input to the mixed phase in the vessel will account for 0.2 to 2 HP cubic meter of ungassed liquid, with preference to a value around 1 $HP/m^3$.

The above described position of end of urea pipe 5 and gaseous ammonia pipes 6 and 16, near blades of impeller 2, provides that urea and gaseous ammonia are fed in the region of the liquid where the mechanical agitation, via said impeller 2, is transferred to the same liquid.

The gaseous phase evolved in vessel 1, due to the reaction products $CO_2$ and $NH_3$, plus the injected excess of $NH_3$, entraining also some melamine and intermediate reaction products, is discharged out via said line 10. The liquid phase from the same vessel 1 is transferred to the second vessel 11, wherein the second stage of conversion takes place. The transfer may be simply done by gravity flow through an overflow pipe 9, while any other means, as a discharge through a level control device or by a transfer pump is intended to be equivalent.

The vessel 11 is also under agitation in fully-baffled conditions by an impeller 12 and baffles 13; volume of the second reaction zone S2 however may be different from volume of first reaction zone S1.

A coil 14 inside vessel 11 is devised to remove heat, controlling the temperature of the vessel content preferably in the range from 310 to 350° C. Said coil 14 follows the same criteria, in connection to the agitator 12, already pointed out for the coil 4. A cooling medium enters the coil 14 via line 17, and exits at line 18.

Ammonia is introduced into vessel 11 by the pipe 16, preferably below the centre of blades of impeller 12 as seen in vessel 1. This results in a very fine subdivision and dispersion of ammonia inside the liquid phase, taking care of recovering melamine by ammination of melamine poly-condensates. At the same time ammonia strips out very efficiently the residual volatile products and carbon dioxide from the melamine melt, which exit the vessel from the overflow pipe 19, or through a level control device, or a transfer pump.

The gas phase evolving from the vessel 11 is discharged via flow line 20, which may equally be connected or not to the line 10 recovering the gas stream from the first vessel 1.

In an alternative embodiment (FIG. 2B), the working pressure of vessel 11 is greater than pressure of vessel 1. A pump 15 is then provided on flow line 9 to raise the pressure of the liquid phase taken from the first vessel 1. The control of the pumping rate may be done by keeping constant the liquid level inside the vessel 1, while the pressure control inside the vessels 1 and 11 is obtained by controlling the gas flows discharged via lines 10 and 20.

In a further alternative (not shown) the cooling heat exchanger 14 is replaced by a melamine melt cooler provided on line 9, ensuring that temperature inside second-stage reactor 11, and then in the second reaction zone, is lower than temperature in the first-stage reactor 1.

Second Embodiment

The process is carried out in a single vessel, in order to compact the equipment and save construction expenses. In particular, the two reaction stages are operated inside two compartments C1 and C2 of a single, horizontal pressure vessel 21. The two compartments C1 and C2 correspond to reaction zones 51 and S2; they may differ in volume, although having the same cross section, by occupying a different length of the horizontal vessel 21. A baffle 22 separates the two compartments, while not closing completely the cross section of the vessel 21 and leaving a relatively small bottom passage 26.

Figure 2B:
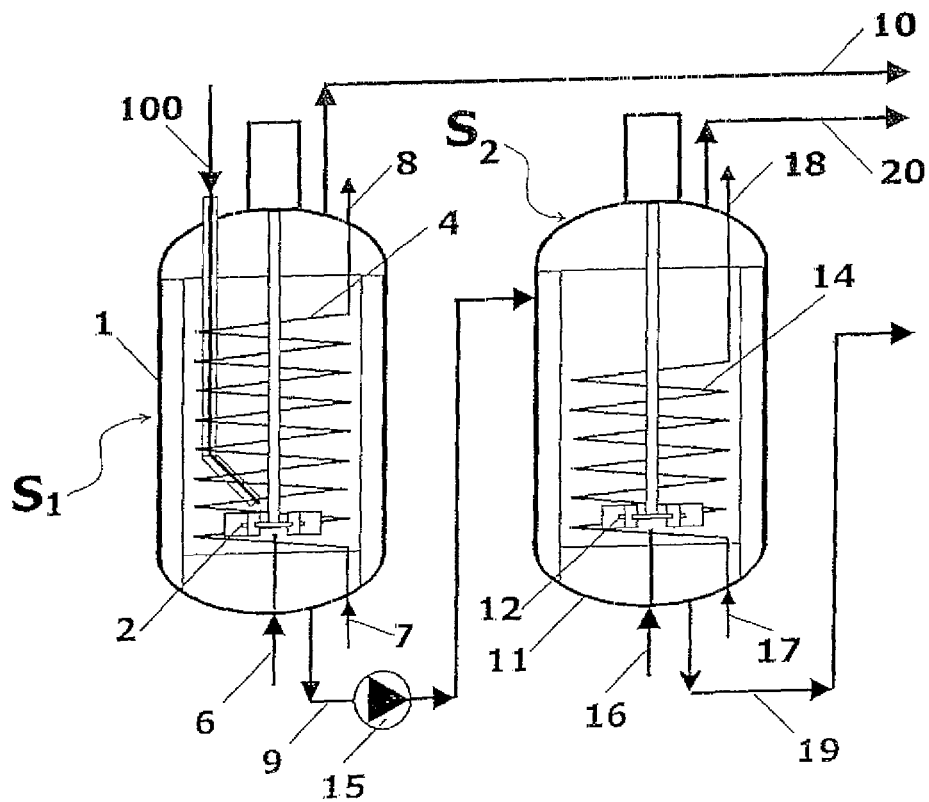
FIG. 2B is a variant of the scheme of FIG. 2A, where the second reactor is operated at a higher pressure than the first reactor.
Figure 3:
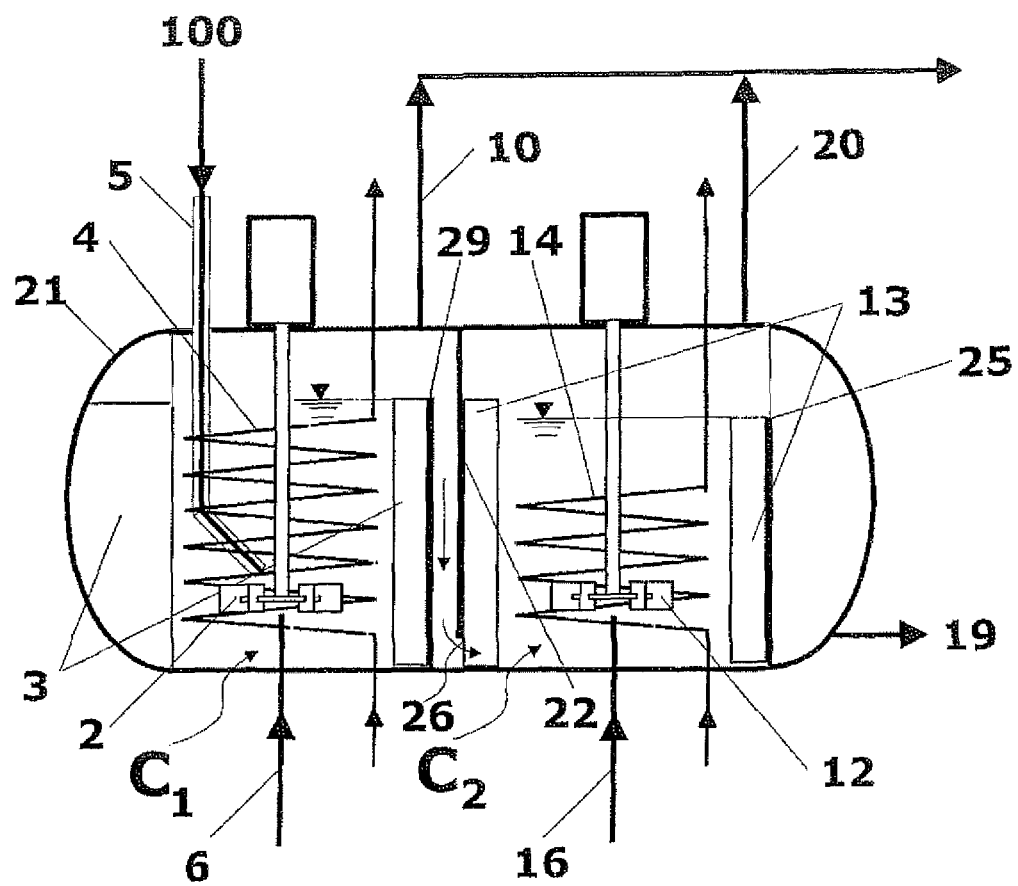
FIG. 3 is a scheme of a second embodiment providing a single, horizontal reactor with two internal stirred compartments.

For the sake of simplicity, items equivalent to those of the first embodiment of FIGS. 2A and 2B are indicated with the same numerals. Each compartment C1, C2 is provided with a mechanical agitator, respectively 2 and 12. Each compartment is also provided with baffles, respectively 3 and 13, to realise the "fully baffled condition" as above described. Heat is supplied to the first compartment C1 by a coil 4, while the second compartment is cooled by a coil 14. Molten urea is fed to the first compartment of the vessel 1 by a jacketed urea pipe 5, with the end port located below and near blades of impeller 4. Ammonia is also fed below the agitator impellers 2, 12 by the pipes 6 and 16.

The melamine melt formed in the first compartment C1 overflows over a weir 29 and passes to the second compartment C2 through said bottom passage 26. After having been cooled by the coil 14, and efficiently contacted with ammonia fed by the pipe 16 in the second compartment C2, in conditions substantially equivalent to those described for FIG. 2A, the liquid product overflows over a weir 25, and is discharged from the vessel 21 by the pipe 19. The gases produced in the two compartments C1 and C2 are collected by means of pipes 10 and 20 and disposed off.

Third Embodiment

In this embodiment, first and the second reaction zones are obtained with multiple stirred reactors arranged in cascade or in series. The advantage is that, at equality of plant production capacity, the same reaction completion is achieved in a reduced total volume of liquid. The number of vessels in series constituting each stage may be conveniently limited to two or three items.

Figure 4:
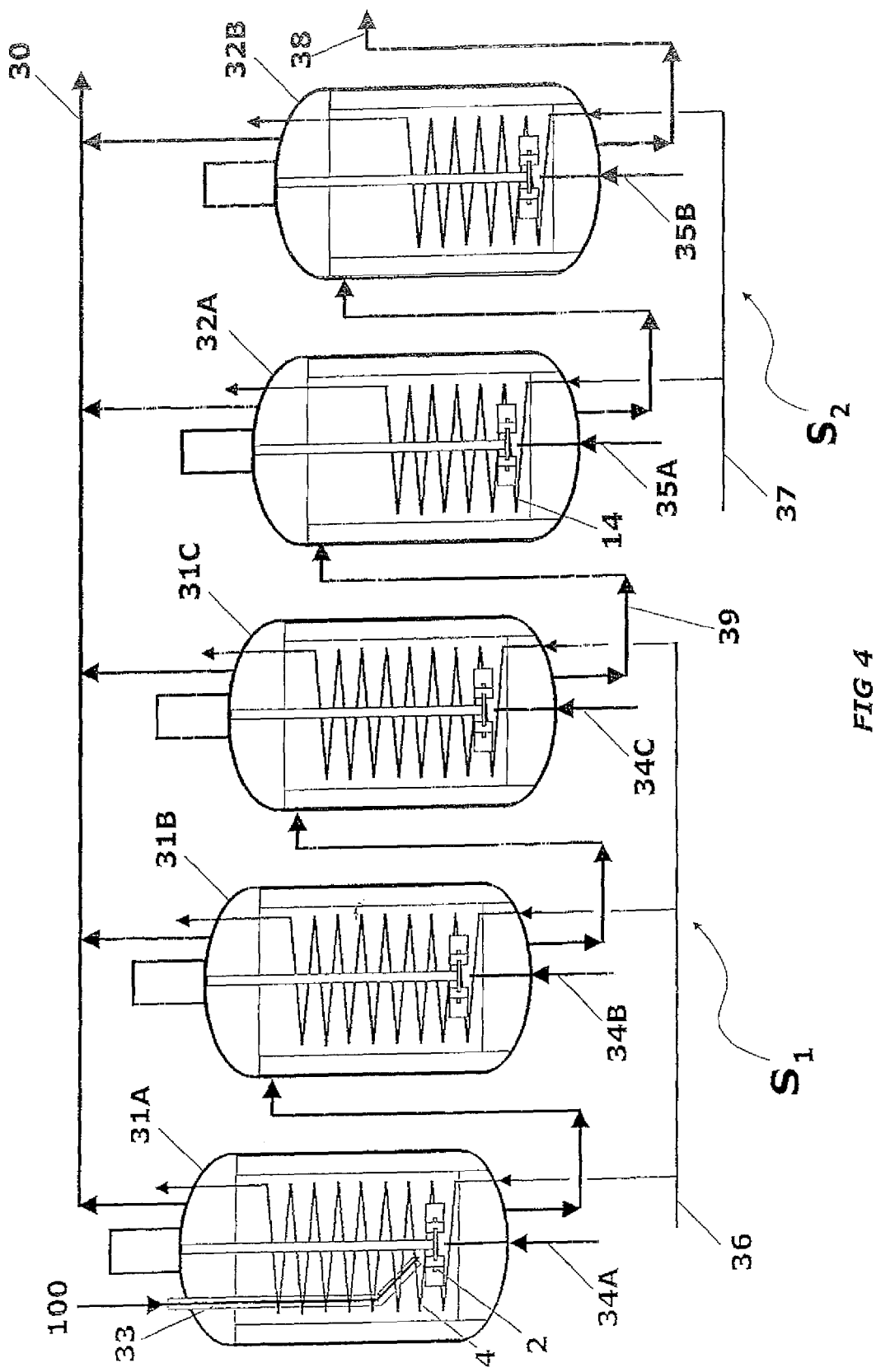
FIG. 4 is a scheme of a third embodiment providing a cascade of stirred reactors.
Figure 5:
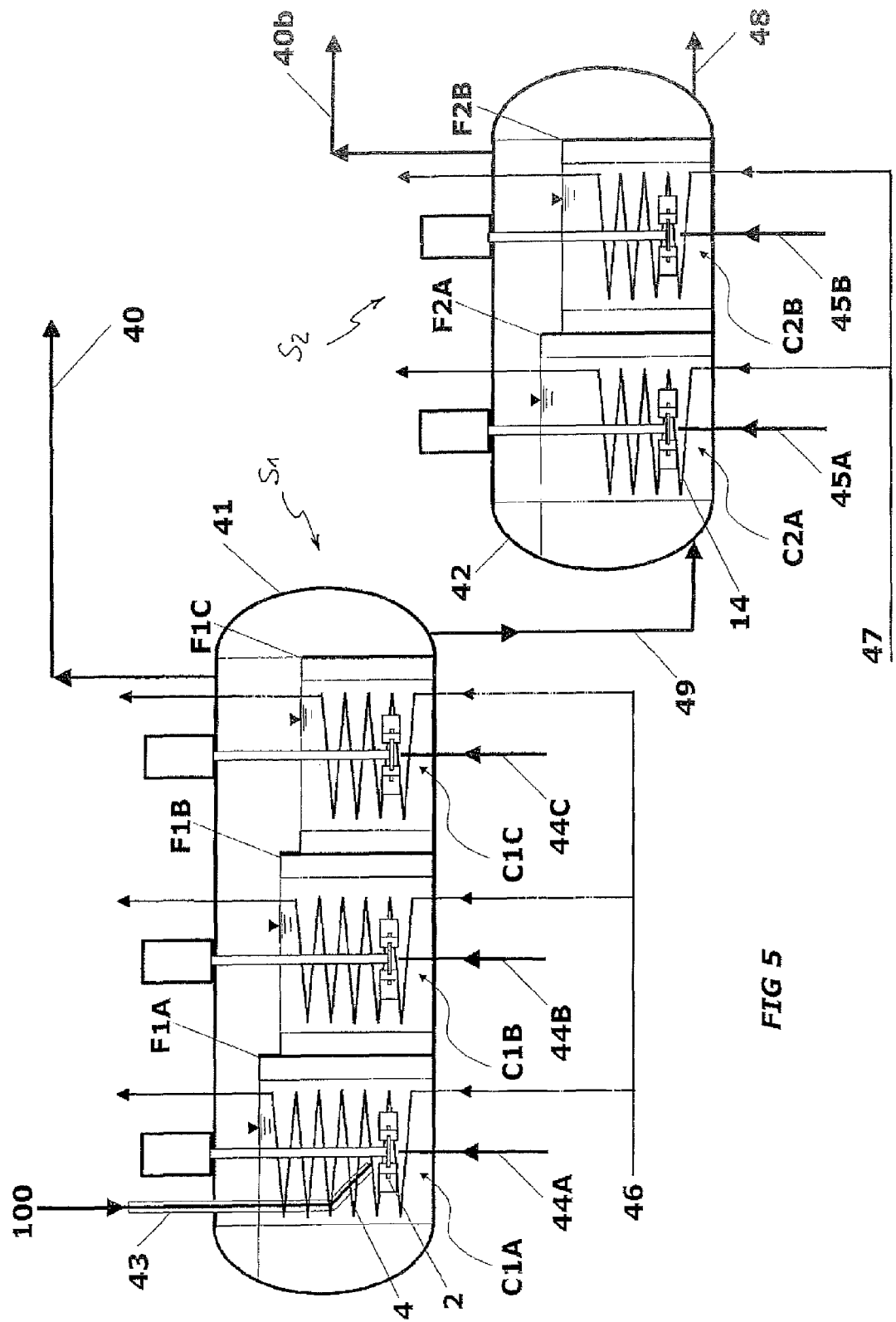
FIG. 5 is a scheme of a fourth embodiment providing two horizontal, multi-compartment stirred reactors.

Referring to example of FIG. 4, a first stage is formed by vessels 31A, 31B and 31C in cascade, and a second stage is formed by two further vessels 32A and 32B also in cascade. The three vessels 31A to 31C provide the first reaction zone S1 and perform the same process as reactor 1 in FIG. 2A; the two vessels of the second stage provide the second reaction zone S2 and perform the same process as reactor 11 in the same FIG. 2A. The molten urea feed 100 enters the first vessel 31A via a pipe 33, while gaseous ammonia is fed and subdivided to all vessels of the series in 34A, 34B, 34C and, respectively, 35A and 35B.

The heating fluid to the first reaction stage is carried in 36, while the cooling fluid to the second stage is available at 37. The end reaction product is discharged by the pipe 38, the off gas is collected by the pipe 30 from all the reactors of the first and second stage. Melamine melt passes form the first stage to the second stage via flow line 39. Intermediate liquid lines are also provided between the reactors of the first and second stage, as shown. All reactors are equipped with a heat exchanger and an impeller, with details according to the first embodiment as above described. FIG. 4 shows the impeller 2 and heating coil 4 of vessel 31A and coil 14 of vessel 32A.

The series of vessels may be realised in form of cascade as in FIG. 4, transferring the liquid from each reactor to the next one by gravity flow, or in series with liquid transfer by other known means such as pumps.

Fourth Embodiment

In this further embodiment, each stirred reactor is a multi-compartmented, horizontal vessel. A cylindrical, horizontal vessel 41, which accomplishes the first reaction stage, is partitioned in consecutive chambers or compartments C1A, C1B and C1C, separated by frames as F1A and F1B allowing the liquid phase to transfer from a chamber to the next one by simple overflow on top of said frames F1A, F1B. Each of said chambers or compartments C1A, C1B and C1C is equipped with a respective impeller 2 for mechanical agitation of the liquid phase.

Molten urea feed 100 enters via urea pipe 43 into the first chamber C1A, while the product is discharged, by overflowing from the last chamber of the vessel. The off gas, which collects from the various chambers in the upper part of the vessel 41, is discharged from the pipe 40. Ammonia is introduced by pipes 44A, 44B and 44C below the impellers of the agitators installed in each compartment, as shown, and is finely dispersed in the liquid phase. Liquid melamine melt is conveyed to the second-stage vessel 42 via line 49. Said second vessel 42 is internally divided in two consecutive chambers by a frame F2A. Ammonia is introduced by pipes 45A and 45B. The liquid end-product is discharged by pipe 48 from the last chamber of vessel 42, while excess ammonia is vented from a pipe 40b.

In a further variant, the second reaction stage can be operated at higher pressure with respect to the first one, by inserting a pump on the line 49.

Fifth Embodiment

In case the two reaction stages are operated at the same pressure, the whole process can be run in a single vessel. An example is shown in FIG. 6, where a horizontal vessel 51 is internally separated into a cascade of consecutive chambers or compartments C1A to C2B as already described in connection to FIG. 4, in order to allow the liquid phase moving from the first to the last chamber by overflowing across degrading weirs.

A frame 55 separates the first-stage compartments C1A to C1C from the second-stage compartments C2A and C2B, leaving a relatively small passage 56 for the liquid phase. Molten urea 100 is fed to the first chamber by a pipe 52, while ammonia is fed in all chambers through pipes 53A, 53B and 53C below the corresponding agitator impellers. A heat supply fluid is distributed to respective heat exchangers of compartments C1A-C1C by the pipe 54A; a cooling fluid is distributed by pipe 54B to heat exchangers of compartments C2A and C2B. The off gas is delivered by a pipe 57, the excess ammonia by 58. The end liquid product is available at 59.

Figure 6:
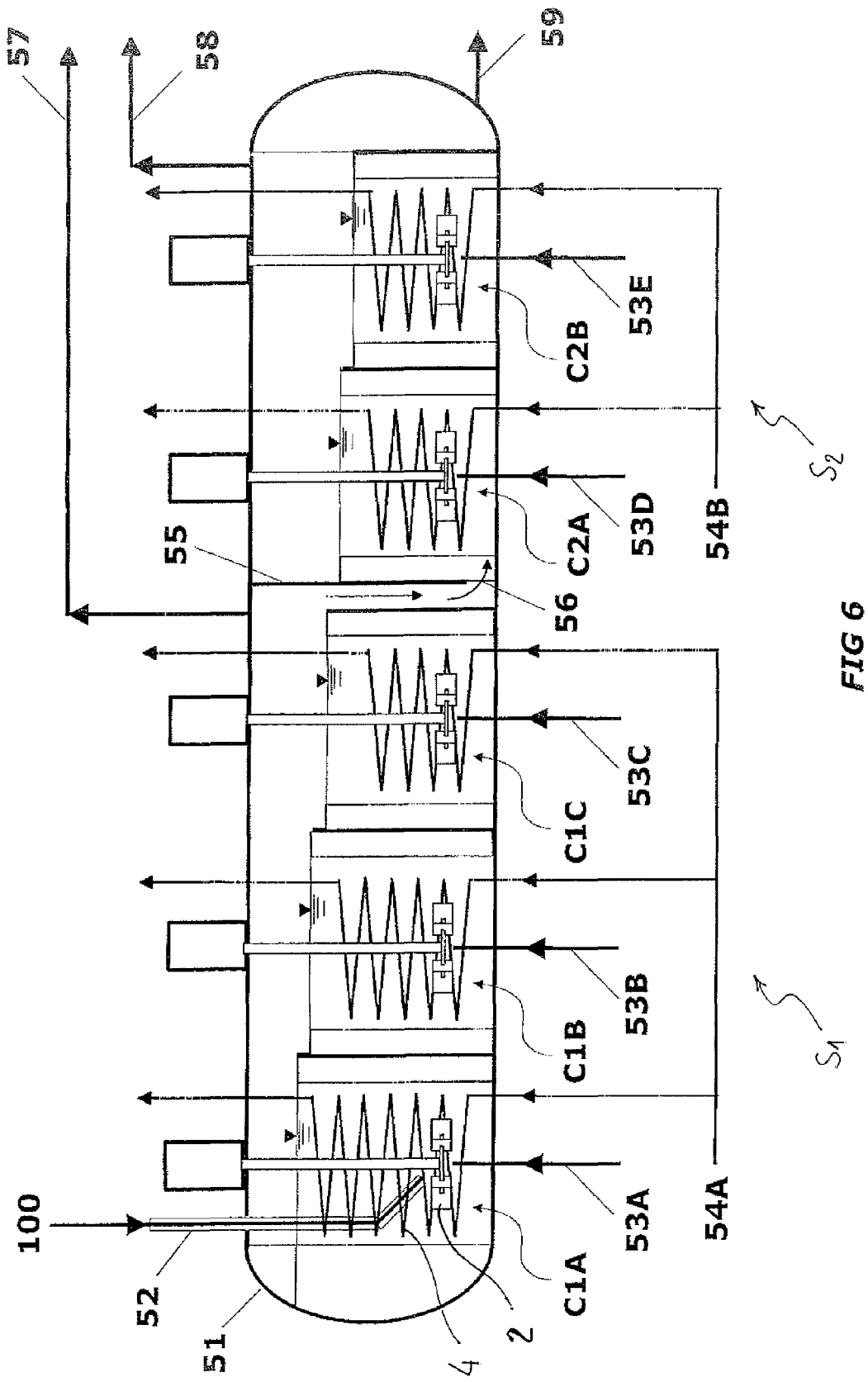
FIG. 6 is a scheme of a fifth embodiment providing a single, horizontal reactor, with multiple compartments for both the first and the second stage of conversion of urea into melamine.

Each compartment of vessel 51 has a respective impeller and heat exchanger, providing heat in the first stage and removing heat in the second stage; for the sake of simplicity, FIG. 6 shows the impeller 2 and heat-exchange coil 4 of the first compartment C1A.

It should be noted that the constructional details disclosed for the first embodiment are applicable also to all other embodiments, as apparent to the skilled person, especially as regards impellers 2, 12 and coils 4, 14. As stated above, further embodiments are possible with any combination of single or multi-compartment vessels.

EXAMPLES

The following detailed examples are intended to better show as the invention may be practiced, and the advantages thereof, but they are not to be interpreted as limiting its scope.

Example 1

A commercial unit, taken as a reference, produces yearly 30,000 tons of melamine. It is based on a urea conversion section composed by three equipment items, namely a main reactor, provided with internal coils supplying the necessary heat to the endothermic reaction of urea, an off-gas scrubber, for the recovery of melamine by the make-up molten urea, a post reactor for the urea conversion completion.

The reactor is an elongated, cylindrical, vertical vessel, having 1300 mm inside diameter, internally provided with:

draft tube, coaxial with the reactor shell, and determining with it an annular space where the heat transfer coils are located, heat transfer coils, constituted by four 2" pipe coil assemblies, each one comprising four coaxial coil banks, for a total of 170 m² heat exchange surface, urea feeding pipe, a deep-pipe with terminal nozzle, of special design to avoid local clogging due to urea tendency to form solid bodies when at high temperature, ammonia sparger, located near the reactor bottom, distributing ammonia at the base of the annular space occupied by the coils, to generate a natural, up-flow circulation of the melamine melt contained in the reactor, which is carried to cross the heat exchange coils, gas disengaging zone, located at the upper end of the vessel, where the off-gas, constituted by ammonia and carbon dioxide, is separated from the melt, which overflows toward the post-reactor vessel.

The total reactor volume is 14.2 m³, of which 11.2 net volume occupied by the liquid phase, so that the residence time calculated as ratio between said net volume and the urea inlet flow of 9.3 m³/h accounts for 1.2 hours. The temperature is 410° C., the pressure is in the range of 100 bar.

The coils are fed with a mixture of molten salts, entering at 470° C.

The post-reactor vessel has a volume of 6 m³, in which the melamine melt coming from the main reactor, evaluated in actual 2.7 m³/h, stays about 2.2 hours, under ammonia bubbling, before being delivered to the next quenching and purification section.

The melamine melt from the reactor has a purity of about 88% by weight, with some 5% un-reacted urea, some 5% melamine precursors and derivatives, the balance being dissolved gases. At the outlet of the post-reactor urea and other organic impurities are approximately halved in concentration.

This reference situation is compared to the results of a demonstration unit, based on the present invention, and following the configuration of FIG. 2A, where the two agitated vessels in series, items 1 and 11, separating into two stages the urea reaction to melamine, may be considered as corresponding to the main reactor and post-reactor of the described commercial plant.

The demonstration was carried out by means of a single vessel, simulating in turn the first and, respectively, the second reaction stage. The characteristics of the vessel:

cylindrical, vertical pressure vessel with dished ends, 1200 mm inside diameter, magnetically driven agitator, axial to the vessel, provided with two six-flat blades turbines, four vertical baffles located at the vessel wall, set at 90° each other, 1" pipe coils on 4 concentric banks for a total surface of 36 m², crossed by molten salts, deep pipe for liquid feed introduction, ending immediately above the upper turbine, in proximity of the agitator shaft, deep pipe carrying ammonia feed immediately below the centre of the lower turbine, solids loading port, located on the top vessel end, vessel vent pipe in correspondence of the vessel upper end, discharging the gaseous phase, overflow pipe, provided with overflow weir, to discharge the liquid product.

The total volume of the vessel was 2.8 m³, while the net volume left to the liquid, after deduction of the coils volume, was 1.9 m³.

While keeping a constant temperature of 410° C. by controlling the molten salt flow, under a pressure of 110 bar controlled by throttling the gas discharge, the urea flow has been stepwise increased, up to obtain, at the reactor outlet, a residual 5% concentration of un-converted urea. In such conditions, 4350 kg of urea, corresponding to 3.6 m³/h, where steady fed to the reactor.

The flow of ammonia, pre-heated at 200° C., was 460 kg/h. The transferred heat flow, with molten salt cooling from 470 to 430° C., was in the range of 1.5 million kcal/h.

After having stopped the reaction, the liquid level dropped, indicating that the steady amount of liquid, under actual agitation conditions, was occupying only the 91.5% of the initial volume, accounting for an actual net liquid volume of 1.74 m³ and demonstrating the existence of an extended interfacial area. The result was that the selected configuration of the agitated reactor is enhancing both heat and mass transfer, reducing the urea residence time, at equality of conversion degree, down to 50% in comparison to the known art.

Example 2

The conversion of urea into melamine was demonstrated in a train of fully baffled reactors in pilot scale.

The reactors train comprised 5 stirred-tank reactors of the same size, each one having the following characteristics:

cylindrical, vertical vessel with dished ends:

design pressure 180 bar, design temperature 430° C.;

internal diameter 700 mm, total volume 600 liters;

vertical agitator based on a single 6 flat-blades turbine rotating at 400 rpm, magnetic drive, 4 baffles located at the vessel wall, and set at 90° each other;

heat exchange surface in form of 1" pipe helical coil, distributed in two co-axial banks for a total of 8 m² heat exchange surface;

piping connections as follows: liquid feed pipe, in form of deep pipe extending inside the reactor until in vicinity of the upper face of the agitator turbine, ammonia feed pipe, ending immediately below the agitator turbine, liquid overflow pipe, determining the level of liquid inside the vessel, gas venting pipe, let-down connection giving the possibility of emptying the vessel, when required;

external electric heating, avoiding the internal reactor wall to cool down below 350-360° C. in case of start-up, or of shut down, or of unsteady operation;

temperature and pressure sensing elements, to provide the output signals allowing the reactor temperature and pressure to be controlled.

The five reactors were connected in cascade, in liquid flow series, as shown in FIG. 4 hereto, this meaning that the liquid overflowing from the first reactor was directly passed by gravity flow to the second reactor, located at a lower level, the liquid from the second to the third one, continuing then with the same modality up to the discharge of the 5$^{th}$ reactor.

The vent connections of the reactors were collected in a common header, ending in a pipe where the pressure control of the system was effected on the resulting stream.

The coils of the first three reactors were connected in parallel to a header distributing a flow of molten salt, delivered to the coils at 470° C. The coils of the last two reactors were connected in parallel to a header distributing molten salt at 340° C.

Molten urea, delivered by a urea producing plant located in the vicinity, was fed to the first reactor, through its inlet deep pipe. Ammonia gas, from the same plant, was fed, under dedicated flow control, and after further preheating, to all 5 reactors, through pipes extending up to the centre of the lower face of each agitator turbine.

In steady-state conditions, with temperature at 400° C. in the second and third reactor, and system pressure at 150 bar, the urea inflow to the first reactor was adjusted to 3000 kg/h. The ammonia flow to each reactor was controlled at 100 kg/h.

The residence time referred to urea was in the range of 10 minutes only per reactor. Notwithstanding the substantially reduced reactor volume, in comparison to the known art, the liquid overflow from the third reactor was demonstrating a complete urea conversion, being practically urea-free by analysis. At the same time the residual reaction intermediates, as oxyamino-triazines, were totally converted to melamine.

With the selected configuration, the melamine melt crossing the last reactors is very efficiently contacted with ammonia by action of the respective mechanical agitators, obtaining the elimination of the residual carbon dioxide by stripping, and a sound recovery of melamine from the poly-condensate compounds, as melem, melam, melon. The temperature approaches the molten salt temperature of 340° C.

With the exemplified reactor train configuration and operating conditions, notwithstanding the relatively short residence time given to the reactant, the obtained melamine melt is rather pure melamine, wherein impurities, included urea, account totally for some tenths of a unit percent only. The melt is ready to supply highly pure melamine after proper solidification in form of crystals, operated following the known separation techniques.

Example 3

A demonstration set up, operating in a scale similar to the preceding example, was realised by means of a horizontal version of fully-baffled reactors in series. The first three reactors have been coupled in a single, horizontal pressure vessel, while additional two reactors constituted the second reactor stage, coupled in a second, single horizontal vessel. The configuration was then as in FIG. 5 hereto, with the difference that a pump was installed between the two consecutive reaction stages, as in FIG. 1B.

Horizontal vessels are of internal diameter 900 mm, and are subdivided into compartments 850 mm long. The first compartment of each vessel has an overflow wire of 750 mm height, while any successive compartment has a wire 25 mm lower.

The 1" coil assembly in the compartments of the first vessel comprises 4 co-axial banks. The total heat exchange surface is 7.3 $m^2$ each compartment. The coils assemblies in the compartments of the second vessel are of two only banks, resulting in a heat exchange surface of 4 $m^2$ each compartment.

The agitator turbine was rotating at 450 rpm, powered by an electric motor.

Baffles of 80 mm width were installed on the vertical partition walls and on the curved walls.

The first stage was operated at 400° C., 100 bar, while the second at 150 bar pressure. The urea melt flow was 3000 kg/h, as in Example 2 above. The molten salt was admitted in parallel to the coils of the first vessel at 470° C., while to the coils of the second vessel at 335° C. The melamine melt was overflowing from the second vessel at about 340° C.

The residence time in the first reaction vessel, calculated as the ratio between the actual, un-gassed liquid volume (1100 liters) and the urea melt volumetric flow (2500 liters/h) was less than half an hour.

Liquid samples from the first reactor and second reactor, notwithstanding the lower pressure in the first stage of the reaction, were very similar to the ones under Example 2 above.

The invention claimed is:

1. A process for converting urea into melamine at a high-pressure and in a liquid phase, where a liquid stream comprising molten urea is fed to a liquid melamine melt, where conversion takes place, the process comprising the steps of:
   feeding said liquid stream comprising molten urea to a first reaction zone, where the melamine melt is kept under mechanical agitation, and a heat input is provided to said first reaction zone;
   taking a liquid phase comprising melamine from said first reaction zone; and
   feeding said liquid phase to a subsequent second reaction zone, where the liquid phase is kept under mechanical agitation, the temperature of the liquid phase in said second reaction zone being lower than temperature of the liquid phase in said first zone.

2. The process according to claim 1, wherein a continuous heat removal is provided from the liquid phase contained in said second reaction zone.

3. The process according to claim 1, wherein the liquid phase is cooled passing from said first reaction zone to said second reaction zone, and said second reaction zone operates in an adiabatic manner.

4. The process according to claim 1, wherein the temperature of the liquid phase in the first reaction zone is in the range from 360 to 440° C., while the temperature of the liquid phase in the second reaction zone is in the range from 320 to 390° C.

5. The process according to claim 1, wherein said second reaction zone is operated at a pressure higher than a pressure of the first reaction zone.

6. The process according to claim 5, wherein the pressure of the liquid phase in the first reaction zone is 50 to 250 bar, while the pressure of the liquid phase in the second reaction zone is 100 to 300 bar.

7. The process according to claim 1, wherein the mechanical agitation in at least one of said first reaction zone and second reaction zone is provided in fully-baffled condition of the liquid phase.

8. The process according to claim 1, wherein gaseous ammonia is added to at least one of the liquid phase of said first reaction zone and the liquid phase of said second reaction zone, said gaseous ammonia being added to the liquid phase in the region where the mechanical agitation is also transferred to said liquid phase.

9. The process according to claim 1, wherein said liquid stream comprising molten urea is also added to the liquid phase in the region where the mechanical agitation is transferred to said liquid phase.

10. An equipment for carrying out a process according to claim 1, said equipment comprising:
    at least one high-pressure vessel or a plurality thereof, defining a first reaction zone and a second reaction zone, and comprising:
    a flow line adapted to feed a liquid stream comprising molten urea to said first reaction zone;
    at least a first mechanical agitator operating in said first reaction zone and heating means adapted to provide heat to said first reaction zone;
    a flow path adapted to receive liquid phase from said first reaction zone and feed said liquid phase to the second reaction zone;
    at least a further mechanical agitator operating in said second reaction zone, and cooling means adapted to provide that temperature of the liquid phase in the second reaction zone is lower than temperature of the liquid phase in the first reaction zone.

11. The equipment according to claim 10, comprising a first stage providing said first reaction zone by means of a first reaction vessel or group of vessels, and a second stage providing said second reaction zone by means of a second vessel or group of vessels, each vessel having a respective internal mechanical agitator and a respective internal heat exchanger for providing or removing heat to/from the liquid phase respectively in vessel(s) of the first and second stage.

12. The equipment according to claim 11, wherein at least one of said vessels of the first stage and/or second stage comprises multiple internal compartments.

13. The equipment according to claim 12, comprising a first-stage vessel with multiple internal compartments arranged in a cascade and providing said first reaction zone, and a second-stage vessel with multiple internal compartments arranged in a cascade and providing said second reaction zone.

14. The equipment according to claim 10, comprising a single pressure vessel, said vessel comprising at least one first-stage compartment providing said first reaction zone and at least one second-stage compartment providing said second reaction zone, the first stage and the second stage being arranged in cascade, each compartment having a respective internal agitator and a heat exchanger for providing or removing heat to/from the liquid phase respectively in vessel(s) of the first and second stage.

15. The equipment according to claim 10, wherein molten urea is fed via a urea pipe with an open end near blades of an agitator in the first reaction zone, and gaseous ammonia is fed via pipes ending near and below the blades of agitators of the first and second reaction zones respectively.

16. The process according to claim 4, wherein the temperature of the liquid phase in the first reaction zone is in the range from 380 to 420° C., while the temperature of the liquid phase in the second reaction zone is in the range from 330 to 350° C.

17. The process according to claim 6, wherein the pressure of the liquid phase in the first reaction zone is 70 to 170 bar, while the pressure of the liquid phase in the second reaction zone is 150 to 250 bar.

* * * * *